United States Patent
Meyer et al.

(10) Patent No.: US 8,308,793 B2
(45) Date of Patent: Nov. 13, 2012

(54) BIFURCATION CATHETER ASSEMBLY WITH DYNAMIC SIDE BRANCH LUMEN

(75) Inventors: Mike Meyer, Richfield, MN (US); Aaron Chalekian, Minneapolis, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 617 days.

(21) Appl. No.: 12/136,304

(22) Filed: Jun. 10, 2008

(65) Prior Publication Data
US 2009/0306758 A1    Dec. 10, 2009

(51) Int. Cl.
*A61F 2/06* (2006.01)

(52) U.S. Cl. ..................................................... 623/1.11

(58) Field of Classification Search .................. 128/898; 604/96.01, 101.01–101.04, 284; 606/108, 606/153, 191–192, 194–195, 198; 623/1.11–1.12, 623/1.23, 1.35
See application file for complete search history.

(56) References Cited

U.S. PATENT DOCUMENTS

| | | | |
|---|---|---|---|
| 5,507,768 A * | 4/1996 | Lau et al. ...................... | 623/1.11 |
| 6,117,140 A * | 9/2000 | Munsinger .................... | 606/108 |
| 6,146,356 A | 11/2000 | Wang et al. | |
| 6,210,429 B1 | 4/2001 | Vardi et al. | |
| 6,325,826 B1 | 12/2001 | Vardi et al. | |
| 6,706,062 B2 * | 3/2004 | Vardi et al. ................... | 623/1.15 |
| 7,220,275 B2 | 5/2007 | Davidson et al. | |
| 2001/0003161 A1 | 6/2001 | Vardi et al. | |
| 2005/0102019 A1 * | 5/2005 | Yadin ............................ | 623/1.11 |
| 2005/0273149 A1 * | 12/2005 | Tran et al. ..................... | 623/1.11 |
| 2008/0086191 A1 | 4/2008 | Valencia et al. | |

FOREIGN PATENT DOCUMENTS

| | | |
|---|---|---|
| WO | 2005122959 | 12/2005 |
| WO | 2006053106 | 5/2006 |
| WO | 2007100672 | 9/2007 |

* cited by examiner

*Primary Examiner* — Ryan Severson
*Assistant Examiner* — Ashley Cronin
(74) *Attorney, Agent, or Firm* — Seager, Tufte & Wickhem, LLC

(57) ABSTRACT

A catheter assembly and related methods having a main balloon, a branch balloon arrangement and a stent. The catheter assembly includes a main catheter branch, a side catheter branch arrangement, and a stent. The main catheter branch includes at least a main balloon and a side balloon. The side catheter branch arrangement includes a branch guidewire housing and a sleeve member. At least a portion of the side catheter branch arrangement extends through a proximal open end of the stent and out through a side branch aperture of the stent. The branch guidewire housing defines a side branch lumen configured to advance over a branch vessel guidewire. The sleeve member is sized to receive the branch guidewire housing, wherein the branch guidewire housing is axially movable within the sleeve member. The sleeve member is typically fixed axially relative to the main catheter branch.

19 Claims, 4 Drawing Sheets

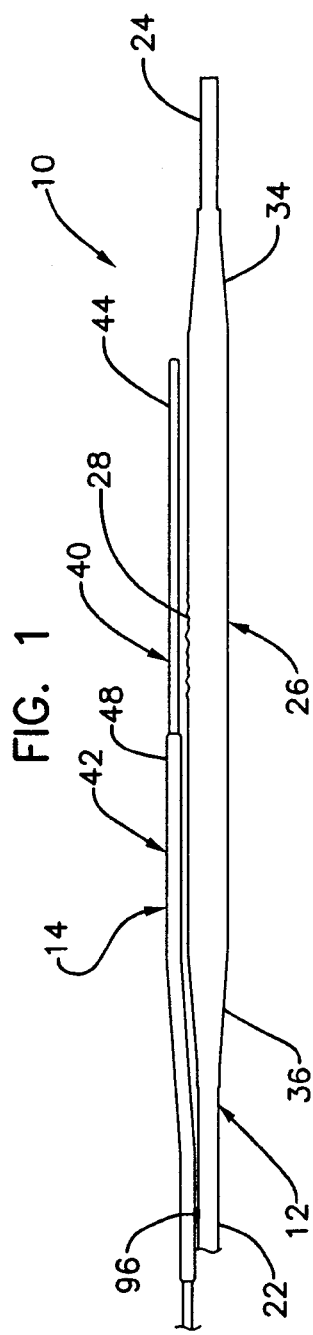
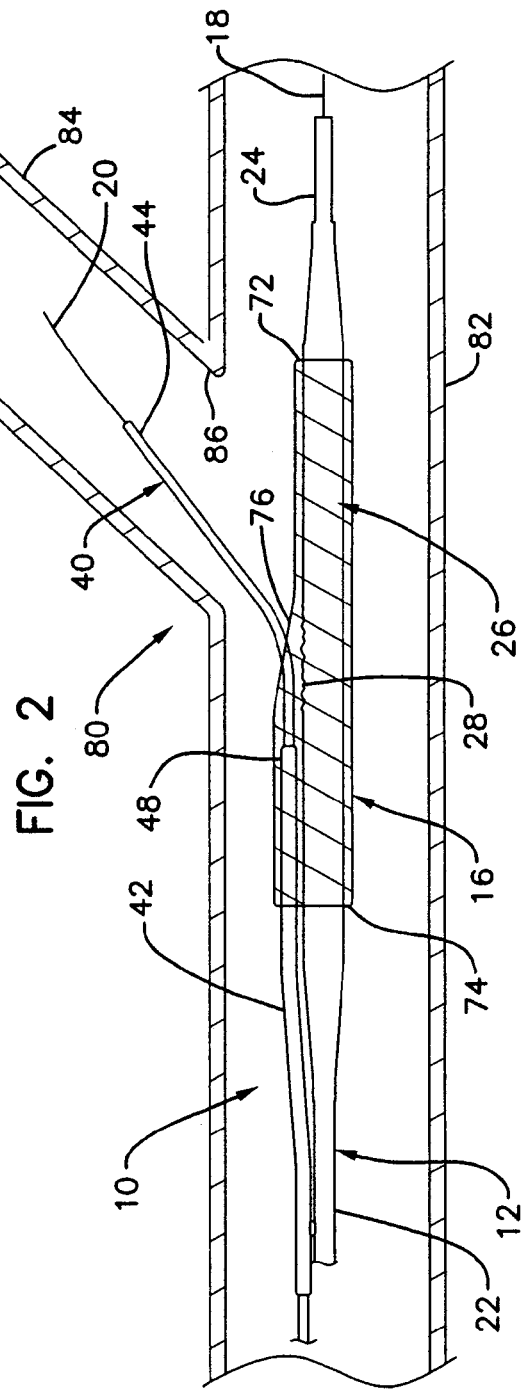

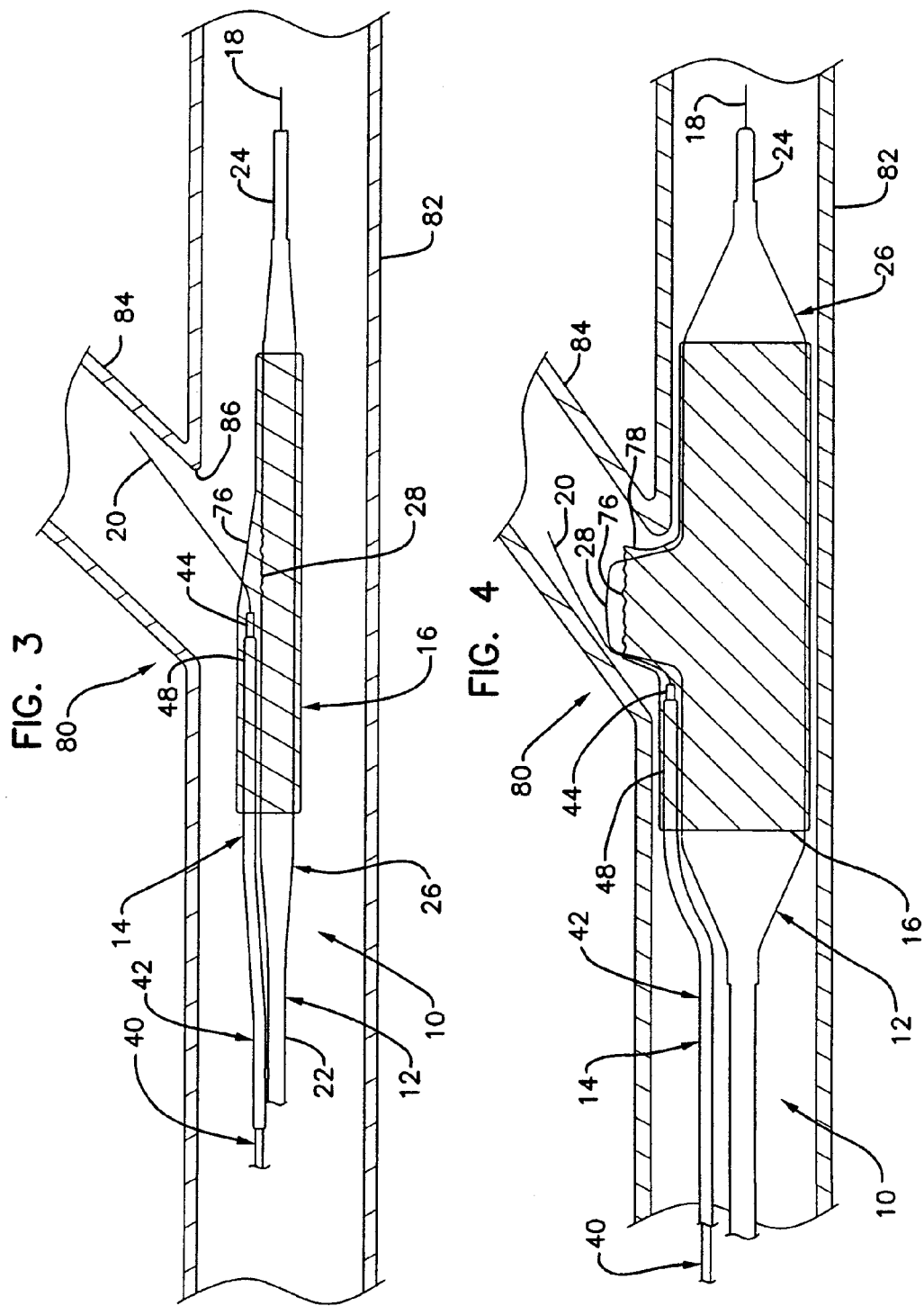

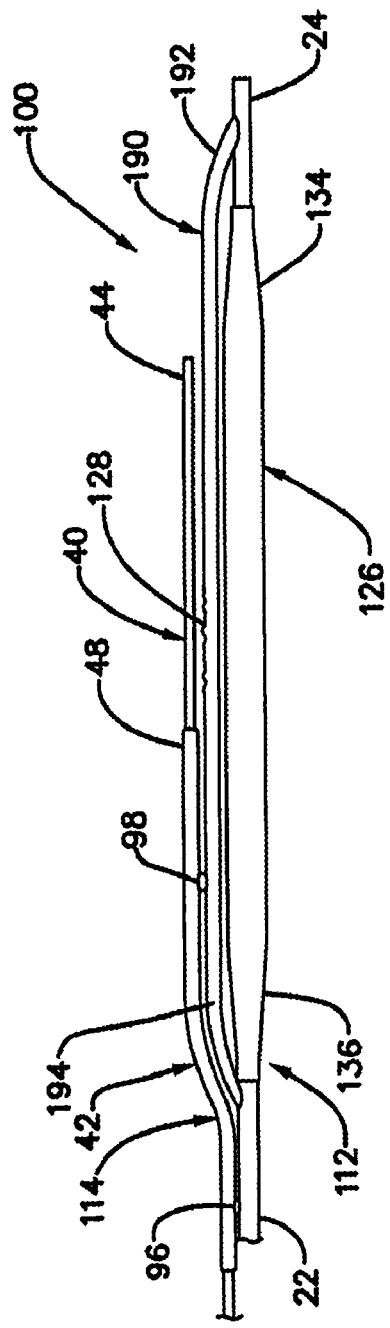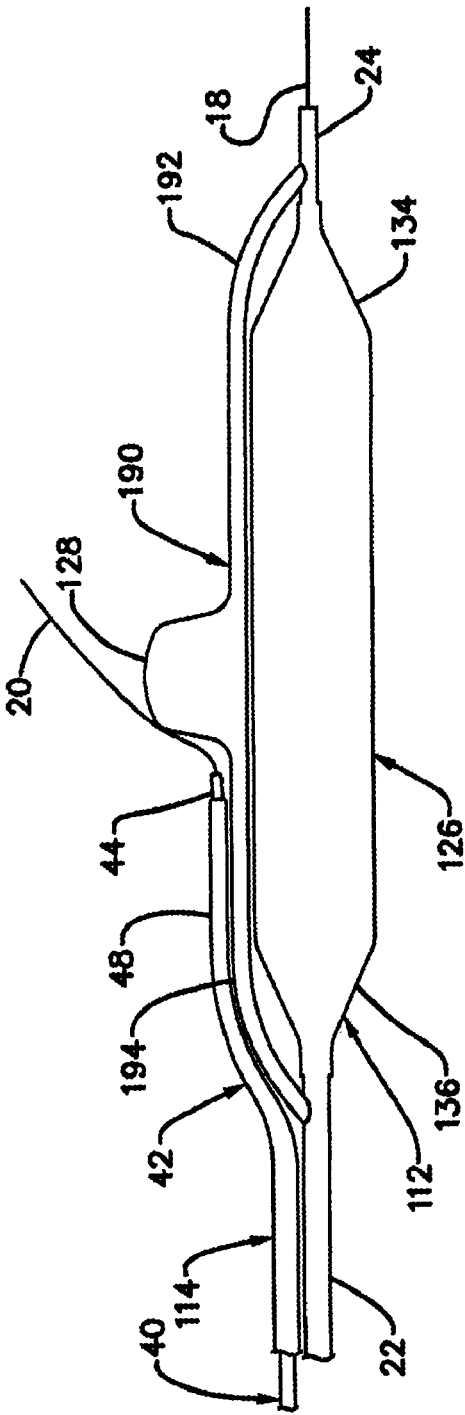

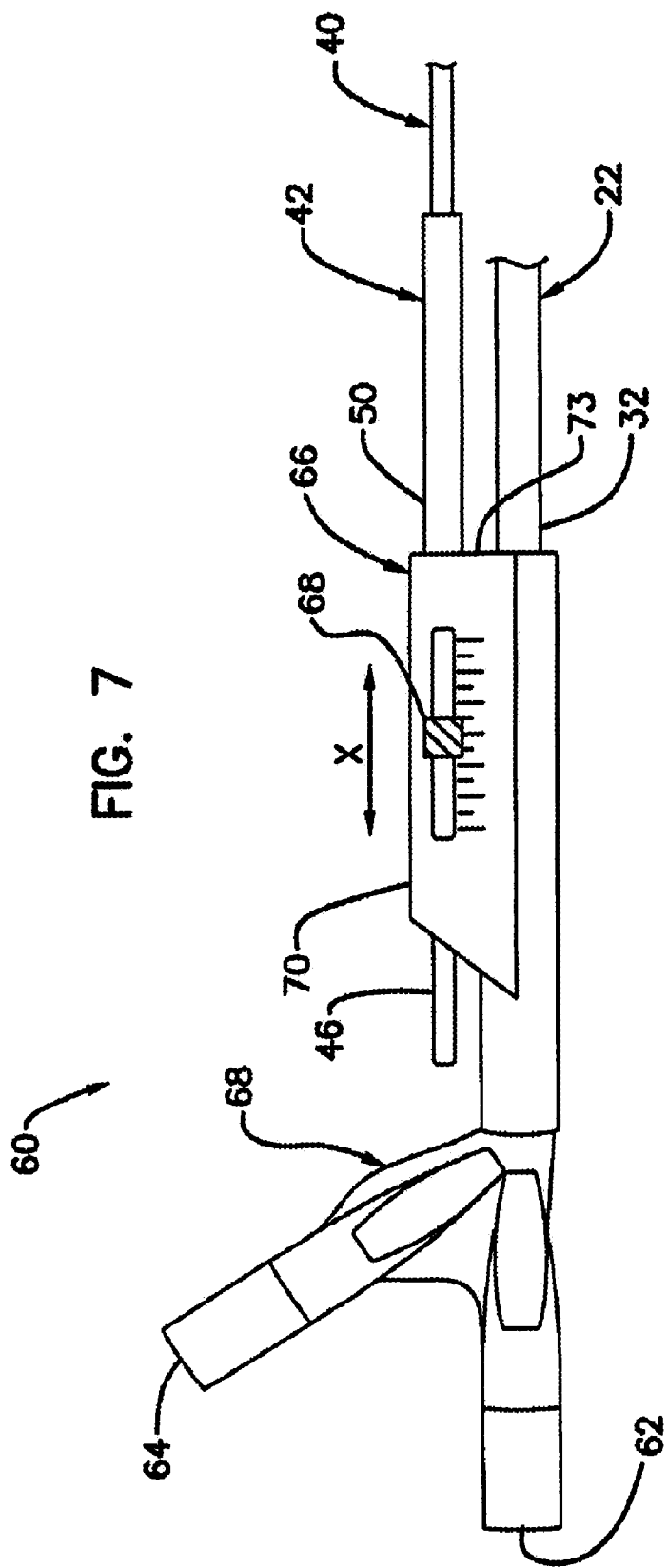

BIFURCATION CATHETER ASSEMBLY WITH DYNAMIC SIDE BRANCH LUMEN

TECHNICAL FIELD

This disclosure relates to catheter assemblies configured for treatment of a vessel bifurcation.

BACKGROUND

Catheters are used with stents and inflatable structures to treat conditions such as strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular shaped body organ for treating conditions such as, for example, occlusions, stenoses, aneurysms, dissections, or weakened, diseased, or abnormally dilated vessels or vessel walls, by expanding the vessels or by reinforcing the vessel walls. Once delivered, the stents can be expanded using one or more inflatable members such as balloons. Stents can improve angioplasty results by preventing elastic recoil and remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed. One challenge related to treatment of a vessel bifurcation involves aligning features of the stent with vessel bifurcation.

SUMMARY OF THE DISCLOSURE

The present disclosure relates to catheter assemblies adapted for use in treating a vessel bifurcation. The catheter assembly can include a main catheter branch, a side catheter branch arrangement, and a stent. The main catheter branch includes at least a main balloon and a side balloon. The side catheter branch arrangement includes a branch guidewire housing and a sleeve member. At least a portion of the side catheter branch arrangement extends through a proximal open end of the stent and out through a side branch aperture of the stent. The branch guidewire housing defines a side branch lumen configured to advance over a branch vessel guidewire. The sleeve member is sized to receive the branch guidewire housing, wherein the branch guidewire housing is axially movable within the sleeve member. The sleeve member is typically fixed axially relative to the main catheter branch.

When treating a vessel bifurcation using the catheter assembly, a main guidewire is positioned in a main vessel and a branch guidewire is positioned in a branch vessel. The main catheter branch is advanced over the main guidewire to a position spanning an opening into the branch vessel. The side catheter branch is advanced over the branch guidewire until the branch guidewire housing is at least partially positioned within the branch vessel. The catheter assembly is adjusted axially and radially to align the side branch aperture of the stent with the opening into the branch vessel. The branch guidewire housing can be advanced or retracted axially (i.e. in a direction parallel with a longitudinal axis of the sleeve member) relative to the sleeve member. The branch guidewire housing can be used to help align features of the stent with the branch vessel. The branch guidewire housing can be retracted out of the branch vessel and proximal of the side branch aperture of the stent prior to expanding the stent to treat the vessel bifurcation.

There is no requirement that an arrangement include all features characterized herein to obtain some advantage according to this disclosure.

BRIEF DESCRIPTION OF THE DRAWINGS

FIG. 1 is a schematic side view of main and side catheter branches of an example catheter assembly in accordance with principles of the present disclosure.

FIG. 2 is a schematic side view of an example catheter assembly positioned at a vessel bifurcation in accordance with principles of the present disclosure.

FIG. 3 is a schematic side view of the example catheter assembly shown in FIG. 2 with a portion of the side catheter branch withdrawn proximally.

FIG. 4 is a schematic side view of the example catheter assembly shown in FIG. 3 with the main and side balloons in an inflated state.

FIG. 5 is a schematic side view of main and side catheter branches of another example catheter assembly with a main balloon and side balloon in a deflated state.

FIG. 6 is a schematic side view of main and side catheter branches shown in FIG. 5 with the main and side balloons in an inflated state.

FIG. 7 is a schematic side view of an example proximal hub member associated with the catheter assemblies shown in FIGS. 1-6.

DETAILED DESCRIPTION

This disclosure relates to bifurcation treatment systems, catheter assemblies, and related methods of treating bifurcations in a patient's body. The term bifurcation means a division location from one unit into two or more units. Generally, two types of bifurcations of a body organ include: 1) a main tubular member defining a main lumen and a branch tubular member defining a branch lumen that extends or branches off from the main tubular member, wherein the main and branch lumens are in fluid communication with each other, and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel).

An example bifurcation is a vessel bifurcation that includes a continuous main vessel and a branch vessel, wherein the vessels define a main lumen and a branch lumen, respectively that are in fluid communication with each other. Alternatively, a vessel bifurcation can include a parent vessel that divides into first and second branch vessels, wherein the vessels define a parent lumen and first and second branch lumens, respectively, which lumens are all in fluid communication with each other.

Example applications of the inventive principles disclosed herein include cardiac, coronary, renal, peripheral vascular, gastrointestinal, pulmonary, urinary, and neurovascular systems. The catheter assemblies, systems and methods disclosed herein can be used for locating a branch vessel of the vessel bifurcation and for placement of a stent relative to the vessel bifurcation for treatment of the vessel bifurcation.

The Example of FIGS. 1-4

Referring now to FIGS. 1-4, an example catheter assembly 10 is shown and described. The catheter assembly 10 includes a main catheter branch 12, a side catheter branch 14, a stent 16, and main and branch guidewires 18, 20. FIG. 1 illustrates the main and side catheter branches 12, 14 with the stent removed for improved clarity. The main catheter branch 12 includes a catheter shaft 22, a main guidewire housing 24, a main balloon 26, and a side balloon 28. The main and side balloons 26, 28 are shown in a deflated state in FIGS. 1-3.

The catheter shaft 22 includes a distal end portion 30 and a proximal end portion 32 (see FIG. 7). The main balloon 26 includes a distal end portion 34 and a proximal end portion 36. The distal end portion 34 is secured to the main guidewire housing 24 at a location distal of the main balloon 26. The proximal end portion 36 is secured to the catheter shaft 22 at a proximal end of the main balloon 26. Typically, the catheter shaft 22 is configured to deliver an inflation fluid to the main and side balloons 26, 28 for inflation of the balloons, and provides for removal of the inflation fluid from the balloons 26, 28 when deflating the balloons.

The side catheter branch 14 includes a branch guidewire housing 40 and a sleeve 42. The branch guidewire housing 40 includes a distal end portion 44 and a proximal end portion 46 (see FIG. 7). The sleeve 42 also includes a distal end portion 48 and a proximal end portion 50 (see FIG. 7). The branch guidewire housing 40 defines a side branch lumen sized to receive the branch guidewire 20. Similarly, the main guidewire housing 24 defines a main branch lumen sized to receive the main guidewire 18. A sleeve 42 defines a sleeve lumen (not shown) sized to receive the branch guidewire housing 40. The branch guidewire housing 40 is axially movable within the sleeve lumen of the sleeve 42.

The term "axially movable" is defined as movement in a direction parallel with a longitudinal axis of the branch guidewire housing 40 or a longitudinal axis of the sleeve 42. The longitudinal axis of and elongate structure such as the branch guidewire housing 40 and the sleeve 42 is typically defined as that axis arranged along a length dimension of the structure, or that axis that extends centrally along a lumen defined by the structure. The term "axially fixed" is defined as maintaining a set or fixed position relative to a longitudinal axis of a structure such as the branch guidewire housing 40 or a longitudinal axis of the sleeve 42. A structure that is "axially fixed" relative to a longitudinal axis can still be moveable in a radial or rotational direction relative to the longitudinal axis.

The branch guidewire housing 40 can extend from the stent 16 proximally to the proximal end portion 32 of the catheter shaft 22. Likewise, the sleeve 42 can extend from the stent 16 proximally to the proximal end portion 32 of the catheter shaft 22. In other arrangements, the sleeve 42 can have a length less than the branch guidewire housing 40 such as, for example, a length in the range of about 5 to about 50 mm. Preferably, the sleeve 42 is positioned at the distal end portion 30 of the catheter shaft 22 at or adjacent to the stent 16 to provide a housing into which the branch guidewire housing 40 can be advanced through and retracted into to provide axial movement relative to the stent 16.

FIGS. 2-4 illustrate the catheter assembly 10 in association with a vessel bifurcation 80. The vessel bifurcation 80 includes a main vessel 82, a branch vessel 84, and an ostium or branch vessel opening 86 that provides access into the branch vessel 84 from the main vessel 82.

Treatment of the vessel bifurcation 80 can be performed with a catheter assembly 10 using various treatment methods and procedures. Typically, the main and branch guidewires 18, 20 are first advanced into the main and branch vessels 82, 84, respectively. After placement of the guidewires 18, 20 in the vessels 82, 84, the proximal end of the guidewires 18, 20 are advanced into distal open ends of the main and branch guidewire housings 24, 40, respectively, and the main and side catheter branches 12, 14 are advanced over the main and branch guidewires 18, 20 to the vessel bifurcation 80.

The stent 16 includes distal and proximal open ends 72, 74, a side branch aperture 76 positioned at a location between the open ends 72, 74, and a plurality of expandable members 78 surrounding and defining the side branch aperture 76. The stent 16 is typically crimped or otherwise secured to the main and side catheter branches 12, 14. When the stent 16 is mounted or otherwise positioned on the main and side catheter branches 12, 18, the side branch aperture 76 is aligned radially and axially with the side balloon 28. When the side balloon is inflated, as will be described in further detail below, the side balloon moves through the side branch aperture 76 to expand the expandable members 78 in a radial outward direction relative to a longitudinal axis of the main catheter branch 12.

The assembly of the main and catheter branches 12, 14 and stent 16 is advanced over the main and branch guidewires 18, 20 to the vessel bifurcation 80. The branch guidewire housing 40 is advanced distally out of the distal end portion 48 of the sleeve 42 a distance that permits the distal end portion 44 of the branch guidewire housing 40 to advance at least partially into the branch vessel 84. The length of that portion of the branch guidewire housing 40 that extends out of the distal end portion 48 of the sleeve 42 can vary depending on several factors including, for example, the location of the distal end portion 48 of the sleeve 42 relative to the stent 16, the dimensions of the stent 16 including, for example, the length of the stent 16, and the dimensions (e.g., length, diameter, material thickness) of features of the main and branch vessels 82, 84. Positioning the distal end portion 44 of the branch guidewire housing 44 at least partially within the branch vessel 84 while the remaining portion of the catheter assembly 10 remains in the main vessel 82 can help in both axial and rotational alignment of the side branch aperture 76 of the stent 16 relative to the ostium 86 of the vessel bifurcation 80. The sliding engagement of the branch guidewire housing 40 within the sleeve 42 can provide certain advantages in treating the vessel bifurcation 80 when the catheter assembly 10 is oriented adjacent the ostium 86.

Typically, the sleeve 42 is axially and radially fixed relative to the main catheter branch 12. In one example, the sleeve 42 is secured to the main catheter branch 12 at a connection point 96 (see FIG. 1), for example at a location proximal of the main balloon 26. One or more connection points 96 can be used at various locations along the length of the sleeve 42 to provide a connection between the main catheter branch 12 and side catheter branch 14. Such connection points can be made using, for example, adhesives, laser bonds, or other heat bonding methods.

Further, the distal end portion 48 of the sleeve 42 can be positioned within the stent 16, for example, at a location proximal of the side branch aperture 76 as shown in FIGS. 2-4. In other arrangements, the distal end portion 48 of the sleeve 42 can be positioned at further proximal locations such as, for example, at the proximal open ends 74 of the stent 16, or at other locations proximal of the stent 16. Locating the distal end portion 48 within the stent 16 and adjacent to the side branch aperture 76 can provide for improved retraction of the branch guidewire housing 40 back into the stent 16 followed by again advancing the branch guidewire housing 40 in a distal direction back out of the stent 16 with minimal catching or otherwise engagement with features of the stent 16 that could inhibit retraction or advancement of the branch guidewire housing 40 relative to the stent 16.

FIG. 2 illustrates the branch guidewire housing 40 positioned at least partially within the branch vessel 84 as part of the treatment step of aligning the side branch aperture 76 with the ostium 86 of the branch vessel. FIG. 3 illustrates the branch guidewire 20 remaining within the branch vessel 84 while the branch guidewire housing 40 is retracted proximally until the distal end portion 44 of the branch guidewire housing 40 is positioned within the stent 16. In other arrangements, the branch guidewire housing 40 can be retracted proximally different distances in comparison to the relative change in position shown in FIGS. 2 and 3. For example, a portion of the branch guidewire housing 40 can remain positioned extending through the side branch aperture 76 of the stent 16 but not within the branch vessel 84, while in other arrangements the distal end portion 44 of the branch guidewire housing 40 is positioned proximal of the distal end portion 48 of the sleeve 42.

In some situations, it is advantageous to proximally retract the branch guidewire housing 40 into the sleeve 42 as part of the process of aligning the side branch aperture 76 of the stent 16 relative to the ostium 86. Such retraction can permit or otherwise facilitate unwinding or untwisting of features of the main and side catheter branches 12, 14 relative to the main and branch guidewires 18, 20. Re-advancing the branch guidewire housing 40 back into the branch vessel 84 alone or in combination with axial and radial movement of the main catheter branch 12 and stent 16 relative to the ostium 86 can further facilitate alignment of the side branch aperture 76 with the ostium 86.

After desired radial and axial alignment of the side branch aperture 76 relative to the ostium 86 is confirmed, the branch guidewire housing 40 can be retracted proximally into the sleeve 42 to a location proximal of the side branch aperture 76 prior to inflation of at least the side balloon 28. Proximally retracting the branch guidewire housing 40 proximal of the side branch aperture 76 can provide benefits in expansion of the expandable members 76 of the stent 16 in a radial outward direction into engagement with the ostium 86 and branch vessel 84 by inflation of the side balloon 28. With the branch guidewire housing 40 removed from within the side branch aperture 76, the side balloon 28 is required to lift only the branch guidewire 20 while expanding the expandable members 78 as opposed to having to lift both the branch guidewire 20 and branch guidewire housing 40 as required in an arrangement in which the branch guidewire housing extends through the side branch aperture 76.

After the stent 16 has been expanded into engagement with the vessel bifurcation 80 and the expandable members 78 moved into a radial outward orientation, the main and side balloons 26, 28 can be deflated and the main and side catheter branches 12, 14 retracted proximally from the stent 16. The main and branch guidewires 18, 20 can remain positioned within the main and branch vessels 82, 84, respectively, for further treatment of the vessel bifurcation 80. For example, a post-dilation balloon catheter can be advanced over the branch guidewire 20 to a position spanning the side branch aperture 76 and then inflated to further expand the expandable members 78 into engagement with the branch vessel 84. In a still further step, a secondary branch stent can be advanced over the branch guidewire 20 to a location positioned within the branch vessel 84 and overlapping at least partially with the expandable members 78, and expanded into engagement with the branch vessel 84 and expandable members 78 to further treat the vessel bifurcation 80.

The Example of FIGS. 5-6

Referring now to FIGS. 5-6, another example catheter assembly 100 is shown and described. The catheter assembly 100 can include a stent 16 having the same or similar structure to the stent 16 shown with reference to FIGS. 1-4. The stent 16 is removed from FIGS. 5 and 6 for purposes of clarity in describing main and side catheter branches 112, 114.

The main catheter branch 112 includes a main balloon 126 and a side balloon assembly 190. The main balloon 126 includes a distal end portion 134 and a proximal end portion 136. The side balloon assembly 190 includes a distal inflation segment 192, a proximal inflation segment 194, and a side balloon 128. The distal inflation segment 192 extends from a connection point at a distal end thereof to a main balloon 126 at the distal end portion 134 of the main balloon 126. A proximal end of the distal inflation segment 192 is coupled in fluid communication with the side balloon 128. The proximal inflation segment 194 is connected in fluid communication with the side balloon 128 at a distal end of the segment 194. A proximal end of the proximal inflation segment 194 is coupled to the main balloon 126 at the proximal end portion 136 of the main balloon 126.

FIG. 5 illustrates the catheter assembly 100 with the main and side 126, 128 in a deflated state. The side catheter branch 114 is secured to the main catheter branch 112 at connection points 96, 98. One or more of the connection points 96, 98 can be defined between the sleeve 42 and the catheter shaft 22 or between the sleeve 42 and the side balloon assembly 190 (e.g., the proximal inflation segment 194). The side catheter branch 114 can be secured to the main catheter branch 112 at a plurality of locations along the length of the sleeve 42. Alternatively, the side catheter branch 114 remains detached from the main catheter branch 112 except at the distal ends thereof when the stent 16 is mounted to the catheter branches 112, 114. Typically, the stent 16 is crimped to the catheter branches 112, 114 thus holding the catheter assembly 100 together until the stent is expanded by inflation of the main and branch balloons 126, 128.

FIG. 5 further illustrates the branch guidewire housing 40 extended distally out of the distal end portion 48 of the sleeve 42. A length of the branch guidewire housing 40 that extends distally out of the sleeve 42 can vary as described above relative to catheter assembly 10. As further described above, the branch guidewire housing 40 can be retracted proximally into the sleeve 42 prior to, for example, inflation of the side balloon 28 as shown in FIG. 6.

Various other arrangements for the side balloon assembly 190 are possible. For example, one of the distal and proximal inflation segments 192, 194 can be detached from the main catheter branch 112. In another arrangement, the proximal inflation segment 194 is secured at its distal end to the side balloon 128 at an off center location on a proximal side of the side balloon 128.

The Example Hub Assembly of FIG. 7

FIG. 7 illustrates a hub assembly 60 for use at a proximal end of the catheter assemblies 10, 100. The hub 60 includes first and second access points 62, 64 for insertion of various components into the catheter shaft 22. For example, the first access 62 can be coupled in fluid communication with an inflation fluid that is advanced into and withdrawn from the catheter shaft 22 for inflation and deflation, respectively, of the main and side balloons of the catheter assemblies 10, 100. The second access 64 can be configured for advancement of a guidewire, such as the main guidewire 18 into the main guidewire housing 24 that is positioned within the catheter shaft 22.

The hub 60 can also include an axial positioning assembly 66 that includes an adjuster 68 and a housing 70. The proximal end portion 50 of the sleeve 42 is mounted to a distal side 73 of the housing 70. The branch guidewire housing 40 extends through the housing 70. In some arrangements, the distal end portion 44 of the branch guidewire housing 40 can extend proximally out of the housing 70. The adjuster 68 is configured to adjust an axial position of the branch guidewire housing 40 relative to the sleeve 42. Axial movement of the adjuster 68 in the axial direction X can move the branch guidewire housing 40 axially relative to the sleeve 42. When the hub 60 is used with the catheter assemblies 10, 100 for treatment of a vessel bifurcation, adjustment of the adjuster 68 can move the branch guidewire housing 40 relative to the branch vessel of the vessel bifurcation and the stent 16.

Various other hub designs and features are possible for use with the side catheter branch arrangements described herein. Some arrangements of the side catheter branch can include a shortened sleeve 42 that does not extend proximally to the hub 60. In such an arrangement, the hub 60 interacts only with the branch guidewire housing 40 of the side catheter branch to move the branch guidewire housing 40 relative to the main catheter branch 12. Other constructions and features are possible for the axial positioning assembly such as different types of adjusters with various capabilities for precise axial movement of the branch guidewire housing 40.

Materials and Other Considerations

The materials used in the balloons, catheter shafts, and edge protect members disclosed herein can be made of any suitable material including, for example, thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and polyetherpolyamide copolymers. One suitable material is Surlyn®, a copolymer polyolefin material (DuPont de Nemours, Wilmington, Del.). Still further suitable materials include thermoplastic polymers and thermoset polymeric materials, poly(ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L21011F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45 D to about 82 D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356. It should be understood that the specific materials disclosed below for the individual embodiments does not limit the embodiment to those materials.

In the example catheter assemblies described above, some of the features can include a lubricious coating on an exterior surface thereof. The coating can promote insertion of the branch balloon into the branch vessel of a vessel bifurcation. The coating can also improve removal of the branch balloon from the branch vessel and the branch aperture of the stent when deflating and removing the catheter assembly from the vessel bifurcation after expansion of the stent. Some example coating for use with the branch balloon include hydrophilic polymers such as polyarylene oxides, polyvinylpyrolidones, polyvinylalcohols, hydroxyl alkyl cellulosics, algins, saccharides, caprolactones, and the like, and mixtures and combinations thereof. Hydrophilic polymers can be blended among themselves or with formulated amounts of water insoluble compounds (including some polymers) to yield coating with suitable lubricity, bonding and solubility. In some examples, portions of the devices described herein can be coated with a hydrophilic polymer or a fluoropolymer such as polytetrafluoroethylene (PTFE), better known as TEFLON®.

While the example stent delivery systems described above illustrate a balloon expandable stent having a predetermined side opening (i.e., branch aperture), other types of stents can be used with the catheter features described above. A variety of stents can be used with the systems and methods disclosed herein. Examples of such stents can be found in U.S. Pat. Nos. 6,210,429 and 6,325,826 to Vardi et al., and U.S. Pat. No. 7,220,275 to Davidson et al., the entire contents of which are incorporated herein by reference. In general, the aforementioned stents have a tubular shape with a continuous sidewall that extends between the proximal and distal ends. Proximal and distal stent apertures are defined at respective proximal and distal ends of the stent. A branch aperture is defined in the sidewall of the stent. The branch aperture provides access between an interior of the stent and an exterior of the stent. In some stents, the branch aperture includes expandable structure around a peripheral edge thereof that expands in a generally radial outward direction relative to a longitudinal axis of the stent. The expandable structure can be configured to extend into the branch lumen of the bifurcation upon expansion of the stent. The stent includes a plurality of strut structures that define the sidewall. The struts are expandable from a first, unexpanded state to a second, expanded state. Typically, the stent is configured to maintain the expanded state. The struts define a plurality of cell openings or cells along a length of the stent. The size and shape of the cells is typically different than the size and shape of the branch aperture. The stent is typically expanded once the stent is properly positioned in the main lumen of the bifurcation with the branch aperture aligned radially and axially with an opening into the branch lumen. The stent, including the expandable structure surrounding the branch aperture, can be expanded with a single expansion or with multiple expansions using, for example, one or more inflatable balloons.

Conclusion

One aspect of the present disclosure relates to a catheter assembly that includes a stent, a main catheter branch, and a side catheter branch arrangement. The stent includes a distal open end, a proximal open end, and a side branch aperture. The side branch aperture is positioned at a location between the distal and proximal open ends. The main catheter branch includes a catheter shaft, a main guidewire housing, a main balloon having a proximal end portion and a distal end portion, and a side balloon positioned at a location between the proximal and distal end portions of the main balloon and extending radially outward relative to the main balloon when inflated. The side catheter branch arrangement includes a sleeve member and a side guidewire housing. The sleeve member defines a sleeve lumen and is fixed axially relative to the main catheter branch. The side guidewire housing defines a guidewire lumen and extends through the sleeve lumen and through the side branch aperture of the stent. The side guidewire housing is adjustable axially relative to the sleeve member.

Another aspect of the present disclosure relates to a catheter assembly that includes a main catheter branch and a side catheter branch arrangement. The main catheter branch includes a catheter shaft, a main guidewire housing, a main balloon having a proximal end portion and a distal end portion, and a side balloon positioned at a location between the proximal and distal end portions of the main balloon. The side balloon is configured to extend radially outward relative to the main balloon when the side balloon is inflated. The side catheter branch arrangement includes a sleeve member defining a sleeve lumen, and a side guidewire housing defining a guidewire lumen. The side guidewire housing extends through the sleeve lumen and is adjustable axially relative to the sleeve member.

A still further aspect of the present disclosure relates to a method of treating a vessel bifurcation with a catheter assembly. The vessel bifurcation includes a main vessel and a branch vessel. The catheter assembly includes a main catheter branch, a side catheter branch, and a stent. The main catheter branch includes a main balloon, a side balloon and a main guidewire housing. The side catheter branch includes a sleeve member and a branch guidewire housing. The branch guidewire housing is arranged to move axially within the sleeve member. The stent includes proximal and distal open ends and a side branch aperture positioned at a location between the proximal and distal open ends. The method includes the steps of advancing the catheter assembly to the vessel bifurcation with the main catheter branch positioned within the main vessel and at least a portion of the branch guidewire housing extending through the side branch aperture of the stent to a position within the branch vessel, aligning the side branch aperture of the stent with an opening into the branch vessel, retracting the branch guidewire housing proximally relative to the sleeve member and out of the branch vessel, and inflating the main and side balloons to expand the stent into engagement with the vessel bifurcation.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A catheter assembly, comprising:
   (a) a stent, the stent having a distal open end, a proximal open end, and a side branch aperture, the side branch aperture positioned at a location between the distal and proximal open ends;
   (b) a main catheter branch, the main catheter branch including:
      i. a catheter shaft;
      ii. a main guidewire housing;
      iii. a main balloon having a proximal end portion and a distal end portion; and
      iv. a side balloon positioned at a location between the proximal and distal end portions of the main balloon and extending radially outward relative to the main balloon when inflated; and
   (c) a side catheter branch arrangement including:
      i. a sleeve member defining a sleeve lumen, the sleeve member being fixed axially relative to the main catheter branch, wherein the sleeve member includes a distal end positioned within the stent; and
      ii. a side guidewire housing defining a guidewire lumen, the side guidewire housing extending through the sleeve lumen and being axially moveable through the sleeve member, the side guidewire housing extending through the side branch aperture of the stent.

2. The catheter assembly of claim 1, wherein the side balloon is integral with the main balloon.

3. The catheter assembly of claim 1, wherein the main catheter branch includes a side balloon arrangement that includes the side balloon, a proximal inflation segment and a distal inflation segment, the proximal and distal inflation segments connected in fluid communication with the side balloon, the proximal inflation segment connected to the catheter shaft at a location proximal of the proximal end portion of the main balloon, and the distal inflation segment connected to the main guidewire housing at a location distal of the distal end portion of the main balloon.

4. The catheter assembly of claim 1, wherein the sleeve member extends from a proximal end portion of the catheter shaft distally to at least the proximal open end of the stent.

5. The catheter assembly of claim 1, wherein the sleeve member has a length less than a length of the catheter shaft.

6. The catheter assembly of claim 1, wherein the side guidewire housing is movable within the sleeve between an extended position wherein a distal end portion of the side guidewire housing is positioned outside of the stent distally beyond the side branch aperture of the stent, and a retracted position wherein the distal end portion of the side guidewire housing is positioned proximal of the side branch aperture of the stent.

7. The catheter assembly of claim 1, wherein the sleeve member is axially fixed relative to the main catheter branch.

8. The catheter assembly of claim 1, further comprising a hub member, the hub member being mounted to a proximal end portion of the main catheter branch and a proximal end portion of the side catheter branch, the hub member configured to slide the branch guidewire housing through the sleeve, thereby adjusting an axial position of the branch guidewire housing relative to the sleeve member.

9. A catheter assembly, comprising:
   (a) a main catheter branch, the main catheter branch including:
      i. a catheter shaft;
      ii. a main guidewire housing;
      iii. a main balloon having a proximal end portion and a distal end portion; and
      iv. a side balloon positioned at a location between the proximal and distal end portions of the main balloon and configured to extend radially outward relative to the main balloon when the side balloon is inflated; and
   (b) a side catheter branch arrangement including:
      i. a sleeve member defining a sleeve lumen; and
      ii. a side guidewire housing defining a guidewire lumen, the side guidewire housing extending through the sleeve lumen and being slidable within the sleeve member;
   (c) a hub member, the hub member being mounted to a proximal end portion of the main catheter branch, wherein a proximal end portion of the side guidewire housing is connected to the hub member, and the hub member configured to slide the side guidewire housing through the sleeve member, thereby adjusting an axial position of the side guidewire housing relative to the sleeve member.

10. The catheter assembly of claim 9, wherein the side balloon is integral with the main balloon.

11. The catheter assembly of claim 9, wherein the main catheter branch includes a side balloon arrangement that includes the side balloon, a proximal inflation segment and a distal inflation segment, the proximal and distal inflation segments connected in fluid communication with the side balloon, the proximal inflation segment connected to the catheter shaft at a location proximal of the proximal end portion of the main balloon, and the distal inflation segment connected to the main guidewire housing at a location distal of the distal end portion of the main balloon.

12. The catheter assembly of claim 9, wherein the sleeve member includes a distal end portion, wherein at least a portion of the distal end portion of the sleeve is positioned within a stent.

13. The catheter assembly of claim 9, wherein the sleeve member is axially fixed relative to the main catheter branch.

14. A method of treating a vessel bifurcation with a catheter assembly, the vessel bifurcation including a main vessel and a branch vessel, the catheter assembly including a main catheter branch, a side catheter branch, and a stent, the main catheter branch including a main balloon, a side balloon and a main guidewire housing defining a first guidewire lumen, the side catheter branch including a sleeve member and a branch guidewire housing defining a second guidewire lumen, the branch guidewire housing arranged to move axially through the sleeve member, the stent including proximal and distal open ends and a side branch aperture positioned at a location between the proximal and distal open ends, the method comprising:

advancing the catheter assembly to the vessel bifurcation with the main catheter branch positioned within the main vessel and at least a portion of the branch guidewire housing extending through the side branch aperture of the stent to a position within the branch vessel;

aligning the side branch aperture of the stent with an opening into the branch vessel;

retracting the branch guidewire housing proximally through the sleeve member and out of the branch vessel; and after the branch guidewire housing is refracted out of the branch vessel, inflating the main and side balloons to expand the stent into engagement with the vessel bifurcation.

15. The method of claim 14, wherein prior to the step of advancing the catheter assembly, the branch guidewire housing extends through the side branch aperture of the stent to a position distal of the side branch aperture, and the step of retracting the branch guidewire housing includes retracting the branch guidewire housing to a position proximal of the side branch aperture of the stent.

16. The method of claim 14, wherein the catheter assembly further includes a hub member positioned at a proximal end of the main and side catheter branches, the retracting step including moving the branch guidewire housing with the hub member axially relative to the main catheter branch and the sleeve member.

17. The method of claim 14, further comprising advancing the branch guidewire housing distally relative to the sleeve member prior to the inflating step.

18. The method of claim 14, wherein the aligning step includes advancing and retracting the branch guidewire housing relative to the sleeve member.

19. The method of claim 14, wherein the main and side balloons are in an uninflated state until after the branch guidewire housing is retracted out of the branch vessel.

\* \* \* \* \*

UNITED STATES PATENT AND TRADEMARK OFFICE
CERTIFICATE OF CORRECTION

| | | |
|---|---|---|
| PATENT NO. | : 8,308,793 B2 | Page 1 of 1 |
| APPLICATION NO. | : 12/136304 | |
| DATED | : November 13, 2012 | |
| INVENTOR(S) | : Mike Meyer et al. | |

It is certified that error appears in the above-identified patent and that said Letters Patent is hereby corrected as shown below:

Column 12
Line 9: delete "refracted" and insert therefor -- retracted --.

Signed and Sealed this
Twenty-second Day of January, 2013

David J. Kappos
*Director of the United States Patent and Trademark Office*